United States Patent [19]
Schönfeld et al.

[11] Patent Number: 5,958,787
[45] Date of Patent: Sep. 28, 1999

[54] POLYMER SENSOR

[75] Inventors: Axel Schönfeld, Wiesbaden; Gernot Feucht, Mutterstadt; Andreas Schleicher, Beselich; Georg Frank, Tübingen; Heinz Rieger, Eppstein, all of Germany

[73] Assignee: Ticona GmbH, Frankfurt, Germany

[21] Appl. No.: 08/836,166

[22] PCT Filed: Nov. 3, 1995

[86] PCT No.: PCT/EP95/04315

§ 371 Date: Jun. 23, 1997

§ 102(e) Date: Jun. 23, 1997

[87] PCT Pub. No.: WO96/14573

PCT Pub. Date: May 17, 1996

[30] Foreign Application Priority Data

Nov. 7, 1994 [DE] Germany ................................. 4439765
Nov. 9, 1994 [DE] Germany ................................. 4440020
Mar. 15, 1995 [DE] Germany ................................. 19509296

[51] Int. Cl.⁶ .......................... G01N 27/00; G01N 29/02; G01N 33/00
[52] U.S. Cl. .......................... 436/116; 422/82.01; 422/88; 73/24.06; 73/24.01; 436/135
[58] Field of Search ........................... 422/82.01, 88, 422/89; 73/24.06, 24.01; 310/313 B, 313 D, 313 R; 436/116, 135

[56] References Cited

U.S. PATENT DOCUMENTS

| | | | |
|---|---|---|---|
| 3,327,519 | 6/1967 | Crawford | 73/23 |
| 3,427,864 | 2/1969 | King, Jr. | 73/24.04 |
| 3,879,992 | 4/1975 | Bartera | 73/24.01 |
| 4,111,036 | 9/1978 | Frechette et al. | 73/24.06 |
| 5,423,902 | 6/1995 | Strutz et al. | 95/273 |
| 5,866,798 | 2/1999 | Schönfeld et al. | 73/24.06 |

FOREIGN PATENT DOCUMENTS

| | | |
|---|---|---|
| 5-99827 | 4/1993 | Japan . |
| 6-129973 | 5/1994 | Japan . |

OTHER PUBLICATIONS

I. Vikholm *Thin Solid Films* 1992, 368–371.

K.H. Karmarkar et al. *Anal. Chim. Acta* 1975, 75, 111–117.

M.S. Nieuwenhuizen et al, *Sensors Actuators* 1987, 11, 45–62.

M.S. Nieuwenhuizen et al. *Fresenius Z Anal. Chem.* 1988, 330, 123–124.

Fog, H.M., *Analytical Chem.* 57:2634–2638 (1985).

Kucera, J.T., et al, *Review of Scientific Instruments* 62: 1630–1632 (1991).

Vikholm, I., *Thin Solid Films* 210:368–371 (1992).

Zhou, R., et al, *Sensors and Actuators B Chem.* B16:312–316 (1993).

*Primary Examiner*—Arlen Soderquist

[57] ABSTRACT

A sensor for oxidizing agents contains an oxidizable aromatic polymer. The sensor comprises a piezoelectric crystal coated with a porous or non-porous layer that contains the oxidizable aromatic polymer.

18 Claims, 1 Drawing Sheet

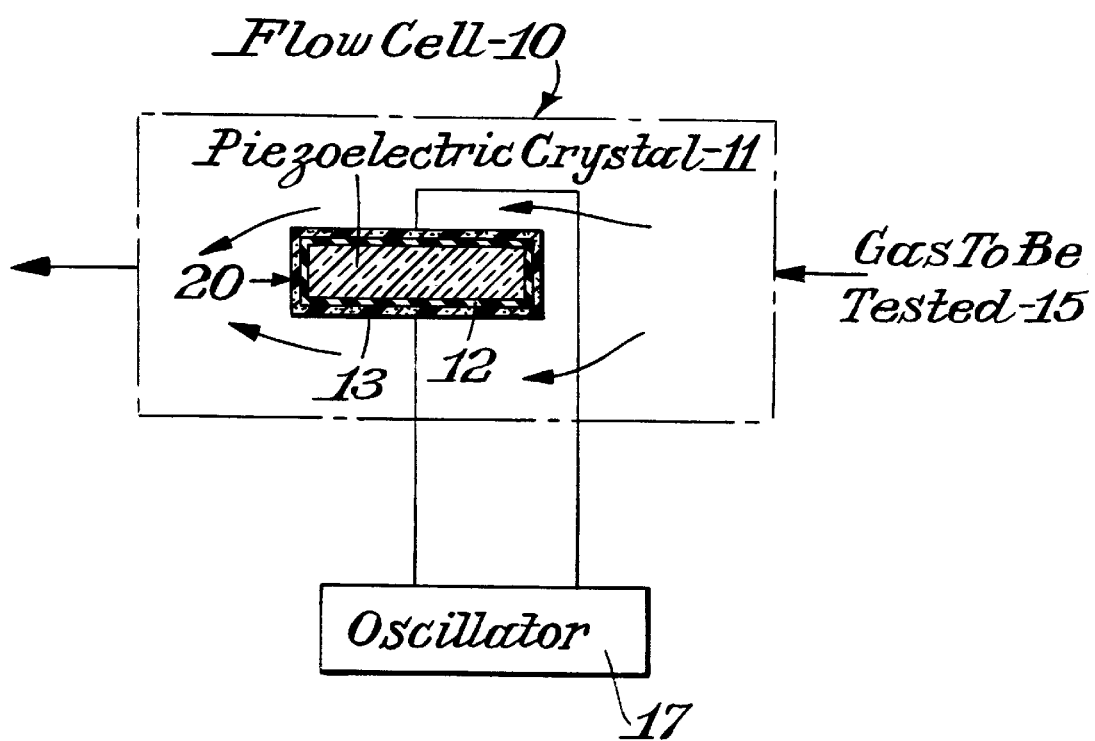

POLYMER SENSOR

This is a National Stage application of PCT/EP95/04315, which has the international filing date of Nov. 3, 1995.

The invention describes a sensor for detecting oxidizing agents, such as oxides of nitrogen ($NO_x$), nitrogen dioxide ($NO_2$), ozone or per acids, the sensor comprising an oxidizable aromatic polymer, such as a polyarylene ether or polyarylene thioether, as the active component.

It is known (Analyt. Chem., 57(13), 2634–8, 1985), that ozone can be detected using a piezoelectric sensor coated with 1,4-polybutadiene. The production of the polymer coating by application with a brush presents a problem in the process described here. The contact surface may be damaged. Moreover, the homogeneity of the layer may not be reproducible by this process, which is confirmed by the stated range of frequency change (2000 to 10000 Hz). Furthermore, the observed frequency changes owing to the ppb quantities of ozone which come into contact are so small that they are of the order of magnitude of the noise of the natural frequency of the piezoelectric crystal (3 to 30 Hz). In addition, the reaction of the ozone with the 1,4-polybutadiene results in the formation of low molecular weight compounds which may partially evaporate. This leads to an opposite change in mass and hence to an error in the determination of the concentration of the gas.

The detection of $NO_2$ in the sub-ppm range in a mixture with pure nitrogen, in which a dual arrangement of the quartz-SAW components (SAW=surface acoustic wave) having a resonant frequency of 600 MHz is used (M. Rapp et al., Sensors Actuators B 1991, 103–108), has also been described. The coating materials used are ultrathin layers (1 to 15 nm) of lead phthalocyanine and iron phthalocyanine derivatives, applied by vapor deposition or by the Langmuir-Blodgett technique. For example, 15 nm thick lead phthalocyanine films permit a limit of detection of 5 ppb for $NO_2$ within a response time of a few minutes.

It is also known that electronic frequency generators for generating oscillations use a piezoelectric element of quartz or PZT ceramic. One of the resonant frequencies is selected for the detection of changes in mass and is amplied by the connected external frequency generator, the oscillation in question in the frequency range up to about 20 MHz being the fundamental oscillation generated by resonance excitation.

In the case of piezoelectric materials, the following function (Sauerbrey equation) is applicable for the frequency change $\Delta f$:

$$\Delta f = -2.3 * 10^6 * F^2 * \Delta m / A$$

in which A is the oscillating surface, F is the fundamental oscillation and $\Delta m$ is the change in mass. If an oscillating surface (for example a quartz disk) is provided with a coating, the frequency of the sensor system changes owing to the increase in mass.

If the coating has absorptive properties, with respect to one or more substances in the surrounding medium, the oscillating system reacts with a change in frequency to the resulting absorption. The properties of the sensor (selectivity, sensitivity, regenerability, cumulability) can be adjusted within wide limits by an appropriate choice of the absorber.

However, it should be noted that the oscillation properties of the piezoelectric materials must not be adversely affected by the coating. Furthermore, the absorber must not react with the substances to be detected, with formation of volatile substances. Furthermore, rapid reaction with the material to be detected is essential for reasonable use.

The oscillatory capability of the piezoelectric crystal is generally lost if the applied absorber on the piezoelectric crystal is crystalline or semicrystalline. However, a prediction is never possible. Even when organic substances are used, the required properties cannot in general be established exactly in a reliable manner. The substance to be used is therefore chosen by a more or less empirical procedure.

It is the object of the invention to avoid the stated disadvantages and to provide a simple and reliable sensor for detecting oxidizing agents, such as ozone, oxides of nitrogen ($NO_x$), nitrogen dioxide ($NO_2$), hydrogen peroxide and per acids.

By using oxidizable aromatic polymers, such as polyarylene ethers or polyarylene thioethers, in sensors, it is possible to obtain sensors, for example for ozone, nitrogen dioxide or other strong oxidizing agents, having high resolution and selectivity.

The invention relates to a sensor for oxidizing agents, which comprises an oxidizable aromatic polymer.

Oxidizable aromatic polymers are aromatic polymers which contain groups, such as sulfide bridges, amino groups, diazo groups, unsaturated bonds, alkyl groups or pendant olefinic groups, which can be oxidized by oxidizing agents.

Preferred oxidizable aromatic polymers are polyarylene ethers or polyarylene thioethers.

BRIEF DESCRIPTION OF THE DRAWING

The sole FIGURE of the Drawing is a schematic representation of a "flow cell" housing a sensor of this invention, illustrating the use of a preferred type of polymer-coated piezoelectric crystal as a sensor for an oxidizing agent.

Polyarylene ethers are polymers which comprise aromatic units bridged by an oxygen atom. Polyarylene ethers are also referred to as polyarylene oxides. Polyarylene oxides are described, for example, in Ullman's Encyclopedia of Industrial Chemistry, 5th Edition, Vol. A21, VCH Publishers, Weinheim 1992, pages 605–614, key word "Poly(Phenylene Oxides), which is hereby incorporated by reference.

Polyarylene thioethers, also referred to as polyarylene sulfides, are polymers which comprise aromatic units bridged via a sulfur atom. Polyarylene thioethers are described, for example, in Ullmann's Encyclopedia of Industrial Chemistry, 5th Edition, Vol. A21, VCH Publishers, Weinheim 1992, page 463–471, key word: Polymers, High-Temperature-5. Poly(Phenylene sulfide), which is hereby incorporated by reference. Polyarylene thioethers containing sulfonyl groups and the preparation of said thioethers are described in Chimia 28 (1974), 567.

The oxidizable aromatic polymer is also referred to below simply as polymer. Oxidizing agents are, for example, ozone, nitrogen dioxide ($NO_2$), oxides of nitrogen ($NO_x$), hydrogen peroxide ($H_2O_2$) inorganic or organic peroxides or per acids, such as peracetic acid.

Oxidizable aromatic polymers are, for example, substituted polyarylenes having repeating units of the general formula (I)

in which $Ar^1$, $Ar^2$, $Ar^3$, $Ar^4$, W, X, Y and Z, independently of one another, are identical or different. The indices n, m, i, j, k, l, o and p, independently of one another, are zero or integers 1, 2, 3 or 4, and their sum must be at least 2; in the formula (I), $Ar^1$, $Ar^2$, $Ar^3$ and $Ar^4$ are o-substituted and unsubstituted arylene systems having 6 to 18 carbon atoms, and W, X, Y and Z are divalent linking groups selected from —$SO_2$—, —S—, —SO—, —CO—, —O—, —$CO_2$— and alkylene and alkylidene groups having 1 to 6, preferably 1 to 4, carbon atoms, and at least one of the linking groups W, X, Y or Z must be an ether bridge.

Preferably used substituents on the aryl ring are $CH_3$, $C_2H_5$, $CH(CH_3)_2$, $C(CH_3)_3$, $C_6H_5$, $OCH_3$, Cl, $CH_3C_6H_5$, 3—$CH_3C_5H_4$, 4—$CH_3C_6H_4$, 4—$(CH_3)_3C_6H_4$ and 2-naphthyl. In addition to the substituents just mentioned, the remaining hydrogen atoms of the aryl systems may, independently of one another, also be replaced by other substituents, such as halogen or amino, nitro or hydroxyl groups. Block copolymers which are composed of units of the formula (I) may also be used.

Preferred polyarylene ethers according to the formula (I) are polyarylene oxides having repeating units of the formula (II)

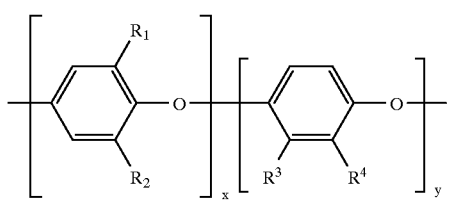

in which the sum of x and y must be 1 and in which in each case zero<x<1 and zero<y<1, and x is zero when y is 1, and vice versa. $R^1$, $R^2$, $R^3$ and $R^4$ are selected from hydrogen, $CH_3$, $C_2H_5$, $CH(CH_3)_2$, $C(CH_3)_3$, $C_6H_5$, $OCH_3$, Cl, $CH_2C_6H_5$, 3—$CH_3C_6H_4$, 4—$CH_3C_6H_4$, 4—$(CH_3)_3C_6H_4$ and 2-naphthyl. $R^1$ to $R^4$ may be identical or different.

Furthermore, polymer blends comprising polyarylene ethers of the formula (II) and polystyrene or polystyrene/styrene mixtures may also be used (Ullmann's Encyclopedia of Ind. Chemistry, Vol. A21, VCH Publishers Inc., New York, 1992).

Polyamide/polyarylene oxide or polyolefin/polyarylene oxide blends may also be used. The content of the polymers of the formula (II) in the blends is from 5 to 99%, preferably from 10 to 99% and in particular from 15 to 99%.

A particularly preferred polyarylene ether is poly-para-[2,6-dimethylphenylene oxide] (PPO) having units of the formula (III)

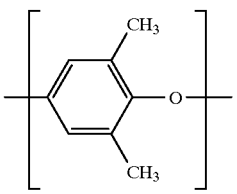

(U.S. Pat. No. 3,306,874) or a polymer blend comprising (PPO) and polystyrene or polystyrene/styrene, which are commercially available.

Preferred polyarylene thioethers are polyphenylene sulfides (PPS) having the repeating unit —$C_6H_4$—S—.

Polyarylene sulfide (PAS) or PPS may also contain up to 50 mol percent of a 1,2- and/or a 1,3-link to the aromatic nucleus. PAS or PPS is understood as meaning both linear and branched or crosslinked material. Furthermore the PAS or PPS may contain, independently of one another, between 1 and 4 functional groups, e.g. alkyl radicals, halogens or sulfonic acid, amino, nitro, cyano, hydroxyl or carboxyl groups, per arylene unit.

Suitable polymers are in general polymers such as polyarylene ethers or polyarylene thioethers, each of which has an average molecular weight $M_w$ of from 2,000 to 2,000,000, preferably from 10,000 to 500,000, in particular from 10,000 to 100,000, determined by GPC.

Those crystals of inorganic or organic substances which exhibit the piezoelectric effect may be used.

Alkaline earth metal titanates, lead/zirconium titanates and quartzes, in particular barium titanate and quartz with the AT section, in which the piezoelectric properties have particularly little temperature dependence, are preferred.

In general, the piezoelectric crystals used have a fundamental oscillation in a frequency range from 20 kHz to 100 MHz, preferably from 0.1 MHz to 50 MHz and in particular from 0.1 MHz to 30 MHz.

If the quartz oscillator is evaluated by the SAW method (SAW=surface acoustic wave) (W. Gopel et al.: Sensors—A Comprehensive Survey, VCH, Weinheim, Germany), it is possible to use piezoelectric crystals whose surface oscillations are in the frequency range from 20 kHz to 1000 MHz.

For example, piezoelectric crystals which are provided with a coating which comprises at least one oxidizable aromatic polymer are suitable as a sensor.

The polymer used or the polymer blend can be applied to one or both sides of the piezoelectric crystals by general coating methods. Coating methods based on polymer or monomer solutions, for example spin coating, dip coating or spray methods, are preferred. All organic substances which dissolve the respective polymer or monomer in a defined temperature range are suitable. Polyarylene ethers are dissolved, for example, in chloroform. For example, caprolactam, 2,4,6-trichlorophenol, preferably isoquinoline, 1-methoxynaphthalene and 1-chloronaphthalene are suitable for dissolving polyarylene sulfides. When a monomer solution is used, the polymerization can be carried out by general surface polymerization techniques, such as laser induction or a temperature increase.

The adhesion of the coating to the sensor surface can be improved by applying an adhesive intermediate layer. The adhesive intermediate layer consists of or contains a polymer having pendant olefinic groups, such as polybutadiene or polyisoprene, polyacrylate, polymethacrylate or polystyrene.

According to the invention, the aftertreatment of the applied polymer layer is effected by drying in commercial drying units, in air, in inert gas or under reduced pressure, at temperatures of 0 to 350° C., preferably 30 to 300° C. and in particular 50 to 300° C. It is also possible to repeat a plurality of coating and drying steps iteratively to achieve thicker polymer layers.

After drying, the amount of coating material on the piezoelectric crystal used is 1 ng/cm$^2$ to 1 mg/cm$^2$, preferably 5 ng/cm$^2$ to 10 mg/cm$^2$ and in particular 10 ng/cm$^2$ to 2 mg/cm$^2$.

The piezoelectric sensor is exposed to the gas to be tested, in a flow cell having a defined volume flow. The sensor frequency is either evaluated directly or is mixed with a stablilized reference frequency and then evaluated (plot of the frequency or of the frequency change against time). By means of downstream processors, the signal change can be converted directly into mass changes and visualized on a display.

The reaction of the sensor to nitric oxide (NO) is small. However, it can be improved if the gas stream to be investigated is passed, before passage over the sensor, through an oxidative inorganic or organic compound which has a redox potential of at least 0.96 V against a standard hydrogen electrode (SHE), for example chloride of lime, sodium hypochlorite, vanadium pentoxide or dichlorodicyanoquinone. These convert the NO into $NO_2$, to which the sensor reacts with high resolution.

It is also possible to determine NO and $NO_2$ alongside one another in the gas mixture by measuring the gas stream on the one hand with the use of preliminary oxidation (measurement of the sum of $NO_2$ and the $NO_2$ formed from NO) and, on the other hand, without preliminary oxidation (measurement of the $NO_2$ without reaction of the NO). The difference between the two measurements gives the respective amounts of NO and $NO_2$ in the gas mixture.

The invention also relates generally to a gas sensor having increased sensitivity and a long life, comprising a piezoelectric crystal in which the surface of the crystal is provided with a porous polymer, a process for its preparation and the use of the sensor for detecting ozone or oxides of nitrogen ($NO_x$). The porous polymer layers may also be used as an active component in sensors operating according to another principle.

By using a porous polymer layer in sensors, a higher sensitivity and longer life of the sensors are obtained.

A porous polymer layer or coating can be produced by two methods. This is described by way of example for a quartz oscillator.

Coating method a.)

In a first step, the quartz oscillator is immersed in a solution of the polymer used for the gas analysis and then, in a second step, in a nonsolvent, until substantially all solvent has been replaced by nonsolvent. The nonsolvent is then removed by drying.

It is possible to use all solvents which dissolve the polymer. Suitable nonsolvents are preferably substances which are readily miscible with the solvent. This results in rapid replacement of the solvent by the nonsolvent (phase inversion), which leads to very porous surfaces. A preferred solvent/nonsolvent combination is, for example, N-methylpyrrolidone/water or tetrahydrofuran/acetone.

Coating method b.)

In a first coating step, the quartz oscillator is immersed in a solution of a polymer which has a strong adhesion effect. After the quartz has been dried, it is immersed, in a second coating step, in suspension of porous particles of the oxidizable aromatic polymer. The quartz is then dried again. Here, it is advantageous to increase the temperature toward the end of the drying—for example to about 10° C. above the glass transition temperature of the polymer of the adhesive intermediate layer—in order to achieve good adhesion of the polymer particles to the polymer of the adhesive intermediate layer, which polymer was applied in the first step. Substances which may be used for the adhesive intermediate layer are all polymers which exhibit good adhesion to the quartz surface. Preferred polymers are those which can be heated above their glass transition temperature in the second drying step, so that good bonding of the porous particles on the quartz oscillator is ensured. Polysiloxane, polyacrylate, polymethacrylate, polystyrene, polyisoprene or polybutadiene may preferably be used. Polymers which also undergo thermal crosslinking on heating and thus result in particularly good adhesion of the porous particles, such as polybutadiene or polyisoprene, are particularly suitable.

The preparation of the porous particles used is described, for example, in German Patent Application P 44 39 478.0, entitled "Filtermaterial auf Polymerbasis zur Entfernung von Komponenten aus Gasen und Flüssigkeiten" [Polymer-based filter material for removing components from gases and liquids], filed on Nov. 8, 1994, which corresponds substantially to U.S. patent Ser. No. 08/836,221, filed Aug. 4, 1997, and which is hereby incorporated by reference.

Porous or nonporous layers of the oxidizable aromatic polymers are particularly suitable for the preparation of sensors for ozone or nitrogen dioxide.

Sensors according to the invention can be used, for example, in the area of work safety, in immission and emission measurements and as filter monitors.

The sensors according to the invention operate in a wide temperature range. In general, the temperature range is from −10 to 100° C., in particular from −10 to 50° C. Higher operating temperatures are possible. Thermostating of the sensors is not required.

Turning now to the Drawing, a "flow cell" 10 houses a sensor 20 of this invention, comprising a piezoelectric crystal 11 coated with an intermediate coating (such as a polybutadiene coating) 12 to which is adhered an outer coating 13 comprising an oxidizable aromatic polymer. In a preferred embodiment, the outer coating 13 is porous (since it contains porous particles). A gas stream to be tested 15 is allowed to flow over the sensor 20, resulting in a frequency change which is tested directly with oscillator 17.

EXAMPLES

1) Commercial HC-18U quartzes (fundamental frequency: 11.5 MHz) were unsoldered from their protective housing and immersed in a 1% strength solution of PPO in chloroform. The sensor was then dried at 70° C. under reduced pressure for 5 hours. The oscillation capability of the coated sensor was tested using a transistorized oscillator, which permits the quartz oscillators to oscillate at from 0.1 to 30 MHz in parallel resonance, and a 10 MHz frequency counter (resolution 0.1 Hz) with a connectable input attenuator and thermostated gating.

Coating with PPO: 32.9 μg (9398 Hz)
$NO_2$ concentration: 600 ppm of $NO_2$ in helium
Flow rate: ~100 l/h

| Time [min] | 0 | 1 | 4 | 5 | 8 | 9 | 12 | 16 | 20 | 21 |
|---|---|---|---|---|---|---|---|---|---|---|
| Δf [Hz] | 0 | 2 | 6 | 14 | 60 | 80 | 124 | 168 | 202 | 210 |
| Time [min] | 24 | 29 | 33 | 37 | 45 | 49 | 57 | 72 | 92 | 132 |
| Δf [Hz] | 230 | 258 | 282 | 300 | 336 | 352 | 380 | 426 | 476 | 558 |

2) Example 1 was repeated with the following characteristics:

Coating with PPO: 111.2 μg (31764 Hz)
$NO_2$ concentration: 600 ppm with $NO_2$ in helium
Flow rate: ~100 l/h

| Time [min] | 0 | 1 | 4 | 5 | 8 | 9 | 12 | 16 | 20 | 21 |
|---|---|---|---|---|---|---|---|---|---|---|
| Δf [Hz] | 0 | 2 | 4 | 32 | 194 | 236 | 302 | 362 | 405 | 416 |
| Time [min] | 24 | 29 | 33 | 37 | 45 | 49 | 57 | 72 | 92 | 132 |
| Δf [Hz] | 436 | 468 | 488 | 504 | 532 | 542 | 564 | 598 | 638 | 700 |

3) Example 1 was repeated with the following characteristics:

Coating with PPO: 18.2 μg (5196 Hz)
$O_3$ concentration: 100 ppb in air
Flow rate: ~100 l/h

| Time [min] | 0 | 21 | 30 | 44 | 60 | 120 | 155 | 238 | 380 |
|---|---|---|---|---|---|---|---|---|---|
| Δf [Hz] | 0 | 2 | 4 | 6 | 10 | 20 | 26 | 38 | 60 |

-continued

| Time [min] | 470 | 600 | 680 | 770 | 830 | 905 | 1010 |
|---|---|---|---|---|---|---|---|
| Δf [Hz] | 70 | 82 | 90 | 98 | 104 | 110 | 118 |

The examples show that both $NO_2$ and ozone are detected virtually linearly by a sensor which contains a polyarylene ether.

4) Commercial HC-18 U quartz (fundamental frequency: 11.5 MHz) were unsoldered from their protective housing and immersed in a 1% strength solution of PPS in isoquinoline. The sensor was then dried at 70° C. under reduced pressure for 5 hours, coating with PPS being 21.1 μg. The oscillation capability of the coated sensor was tested with a transistorized oscillator, which permits quartz oscillators to oscillate at from 0.1 to 30 MHz in parallel resonance, and a 10 MHz frequency counter (resolution 0.1 Hz) with a connectable input attenuator and thermostated gating. The sensor was brought into contact with an $NO_2$-containing gas stream. $NO_2$ concentration: 600 ppm of $NO_2$ in helium, flow rate: ~100 l/h

| Time [min] | 0 | 20 | 25 | 31 | 37 | 41 | 47 | 51 | 58 | 63 |
|---|---|---|---|---|---|---|---|---|---|---|
| Δf [Hz] | 0 | 74 | 84 | 90 | 100 | 112 | 120 | 126 | 140 | 144 |
| Time [min] | 68 | 78 | 88 | 98 | 108 | 128 | 158 | 188 | 218 | 267 |
| Δf [Hz] | 152 | 162 | 178 | 196 | 208 | 240 | 274 | 304 | 330 | 450 |

The example shows that $NO_2$ is virtually linearly detectable by the sensor which contains a sulfur-containing polymer.

5) Sensor with porous coating according to Method a.) Commercial quartzes were removed from their protective housing and immersed in a 1% strength solution (sensor 1) and in a 5% strength solution (sensor 2) of PPO in N-methylpyrrolidone (NMP). The quartzes, to whose surface a film of NMP solution adheres, were then immersed directly in distilled water. After one minute, the quartz was removed again and dried, the oscillation capability was then checked and the new oscillation frequency was measured.

The mass of the coating was determined from the frequency difference using the Sauerbrey equation. (cf. page 2). An ozone-containing gas stream was allowed to flow over the quartzes in a cell. The frequency change was tested directly with a transistorized oscillator, which permits quartz oscillators to oscillate between 0.1 and 30 MHz in parallel resonance, and a 10 MHz frequency counter with a connectable input attenuator and thermostated gating.

Example 5.1

Sensor with Porous Layer

Coating with PPO: 19.23 µg
Ozone concentration: 500 ppb
Flow rate: ~100 l/h

| Time [min] | 200 | 450 | 600 | 750 | 840 | 900 | 1200 | 1500 | 1800 | 2100 | 2520 | 3000 | 3300 | 3600 | 3900 |
|---|---|---|---|---|---|---|---|---|---|---|---|---|---|---|---|
| Δf [Hz] | 84 | 132 | 180 | 228 | 264 | 284 | 368 | 476 | 568 | 672 | 812 | 976 | 108 | 1164 | 1276 |

Example 5.2

Sensor with Porous Layer

Coating with PPO: 117.83 µg
Ozone concentration: 500 ppb
Flow rate: ~100 l/h

| Time [min] | 200 | 450 | 600 | 750 | 840 | 900 | 1200 | 1500 | 1800 | 2100 | 2520 | 3000 | 3300 | 3600 | 3900 |
|---|---|---|---|---|---|---|---|---|---|---|---|---|---|---|---|
| Δf [Hz] | 304 | 640 | 756 | 932 | 1004 | 1048 | 1268 | 1428 | 1572 | 1740 | 1968 | 2216 | 2344 | 2468 | 2588 |

6) Sensor with porous particles according to Method b.) Commercial quartzes were removed from their protective housing and immersed in a 1% strength solution of polybutadiene in toluene. The quartzes were then dried and the frequency change measured. The sensors provided with the thin polybutadiene layer were then immersed at 25° C. in a 1% strength suspension of PPS and 1-methoxynaphthalene and the quartzes were dried again. After evaporation of the solvent, the temperature was increased to 100° C. for about 30 minutes and the frequency change was measured again.

An ozone-containing gas stream was allowed to flow over the coated quartzes in a cell. The frequency change was tested directly with a transistorized oscillator, which permitted quartz oscillators to oscillate between 0.1 and 30 MHz in parallel resonance, and a 10 MHz frequency counter with a connectable input attenuator and thermostated gating.

Example 6.1

Sensor with Porous Particles

Coating with polybutadiene: 4.3 μg
Coating with PPS: 35.16 μg
Ozone concentration: 100 ppb
Flow rate: ~100 l/h

| Time [min] | 0 | 3 | 8 | 11 | 19 | 42 | 70 | 98 | 120 | 149 | 190 | 213 | 254 | 284 | 301 |
|---|---|---|---|---|---|---|---|---|---|---|---|---|---|---|---|
| Δf [Hz] | 0 | 4 | 20 | 28 | 54 | 118 | 188 | 242 | 282 | 332 | 402 | 448 | 494 | 522 | 536 |

Example 6.2

Sensor with Porous Particles

Coating with polybutadiene: 2.26 μg
Coating with PPS: 33.74 μg
Ozone concentration: 200 ppb
Flow rate: ~100 l/h

| Time [min] | 0 | 3 | 4 | 5 | 7 | 10 | 13 | 15 | 20 | 25 | 31 | 40 | 45 | 46 | 47 |
|---|---|---|---|---|---|---|---|---|---|---|---|---|---|---|---|
| Δf [Hz] | 0 | 20 | 35 | 50 | 72 | 96 | 132 | 144 | 168 | 196 | 220 | 248 | 256 | 262 | 270 |

Example 6.3

Sensor with Porous Particles

Coating with polybutadiene: 1.92 μg
Coating with PPS: 20.82 μg
Ozone concentration: 1 ppm
Flow rate: ~100 l/h

| Time [min] | 0 | 2 | 3 | 5 | 7 | 10 | 12 | 15 | 17 | 20 | 25 | 30 | 40 | 50 | 60 |
|---|---|---|---|---|---|---|---|---|---|---|---|---|---|---|---|
| Δf [Hz] | 0 | 76 | 142 | 220 | 304 | 380 | 428 | 492 | 520 | 554 | 596 | 630 | 678 | 712 | 734 |

The examples described above show that an increasing frequency change can be observed with increasing concentration, and even concentrations of 100 ppb (Example 6.1) can still be readily measured. A very long life is also found (Examples 5.1 and 5.2: 3900 min).

We claim:

1. A sensor for oxidating agents, which comprises a piezoelectric crystal having a plurality of layers on a surface thereof, including an intermediate layer and an outer layer, said outer layer comprising at least one oxidizable aromatic polymer.

2. The sensor as claimed in claim 1, wherein said outer layer comprises porous oxidizable aromatic polymer particles.

3. The sensor as claimed in claim 1 wherein a said intermediate layer comprises a polymer having pendant olefinic groups or polybutadiene, polyisoprene, polyacrylate, polymethacrylate, polystyrene or polysiloxane.

4. The sensor as claimed in claim 1, wherein said piezoelectric crystal is an alkaline earth metal titanate crystal, a lead zirconium titanate crystal or a quartz crystal.

5. The sensor as claimed in claim 1, wherein a said oxidizable aromatic polymer is a substituted polyarylene having repeating units of the general formula (I)

in which

Ar$^1$, Ar$^2$, Ar$^3$, Ar$^4$, W, X, Y and Z, independently of one another, are identical or different; Ar$^1$, Ar$^2$, Ar$^3$ and Ar$^4$ are o-substituted or unsubstituted arylene groups having 6 to 18 carbon atoms, and W, X, Y and Z are —SO$_2$—, —S—, —SO—, —CO—, —O—, —CO$_2$— or alkylene or alkylidene having 1 to 6 carbon atoms; and the indices n, m, i, j, k, l, o and p, independently of one another, are zero or a number from 1 to 4, and their sum must be at least 2.

6. The sensor as claimed in claim 5, wherein at least one of the groups W, X, Y or Z is —O— or —S—.

7. The sensor as claimed in claim 5, wherein the layer comprising at least one oxidizable aromatic polymer comprises a porous coating.

8. The sensor as claimed in claim 5, wherein a said oxidizable aromatic polymer is oxidized, sufficiently for gas analysis purposes, by ozone, an oxide of nitrogen, a peroxide or a per acid.

9. The sensor as claimed in claim 1, wherein said oxidizable aromatic polymer is a sulfur-containing polymer or a polyarylene ether.

10. The sensor as claimed in claim 9, wherein said sulfur-containing polymer is a polyarylene thioether.

11. The sensor as claimed in claim 10, wherein said polyarylene thioether is a linear or branched polyphenylene sulfide.

12. The sensor as claimed in claim 9, wherein said polyarylene ether comprises poly-p-(2,6-dimethylphenylene oxide).

13. A gas analysis device comprising a flow cell containing gas sensor as claimed in claim 1 and an oscillator in a direct testing relationship with said gas sensor.

14. A method for analyzing for an oxidizing agent comprising the step of bringing the oxidizing agent into contact with a sensor as claimed in claim 1.

15. The method as claimed in claim 14, wherein the oxidizing agent is ozone, a nitrogen oxide, a peroxide or a per acid.

16. A process for the preparation of a gas sensor for gas analysis from a piezoelectric crystal, said process comprising:

a) immersing the crystal in a solution containing a oxidizing agent-sensing polymer and a solvent therefor;

b) immersing the thus-immersed crystal in a nonsolvent for said oxidizing agent-sensing polymer until substantially all of said solvent has been replaced by said nonsolvent, and c) removing said nonsolvent by drying such that said oxidizing agent-sensing polymer remains on the surface of the crystal in porous form.

17. A process for the preparation of a gas sensor for gas analysis from a piezoelectric crystal, said process comprising.:

a) immersing the crystal in a solution containing a polymer having an adhesive action, b) drying the thus-immersed crystal, c) immersing the thus-dried crystal in a suspension containing porous particles of an oxidizing agent-sensing polymer, and d) drying the thus-immersed crystal until said porous particles are bonded to surfaces of the crystal by an intermediate layer comprising said polymer having an adhesive action.

18. The process as claimed in claim 17, wherein said polymer having an adhesive action is polybutadiene, polyisoprene, polyacrylate, polymethacrylate, polystyrene or polysiloxane.

* * * * *